United States Patent [19]

Seng et al.

[11] 4,033,960
[45] July 5, 1977

[54] 2-MERCAPTOQUINOXALINE-DI-N-OXIDE PRODUCTS AND A METHOD FOR THEIR PREPARATION

[75] Inventors: Florin Seng, Schildgen; Kurt Ley, Odenthal-Gloebusch, both of Germany

[73] Assignee: Bayer Aktiengesellschaft, Germany

[22] Filed: Dec. 9, 1975

[21] Appl. No.: 639,084

Related U.S. Application Data

[62] Division of Ser. No. 491,226, July 24, 1974, abandoned.

[30] Foreign Application Priority Data

July 31, 1973   Germany .................... 2334722

[52] U.S. Cl. ............... 260/250 QN; 260/250 Q; 424/250
[51] Int. Cl.$^2$ ..................................... C07D 241/52
[58] Field of Search ................. 260/250 Q, 250 QN

[56] References Cited

UNITED STATES PATENTS

| | | | |
|---|---|---|---|
| 2,421,031 | 5/1947 | Mahan | 260/551 |
| 3,609,151 | 9/1971 | Seng et al. | 260/250 |

OTHER PUBLICATIONS

Katritzky, "Chemistry of the Heterocyclic N–Oxides", Academic Press, London, 1971, pp. 168, 209, 212–215.
Issidorides et al., J. Org. Chem., 31, 4007 (1966).
Girges et al., Chem Abs. 76, 24933b (1972).
Bercot–Vatteroni, Theilheimer's, "Synthetic Methods of Organic Chem.", 19, No. 378 (1962).
Yamada et al., Theilheimer's, "Synthetic Methods of Organic Chemistry", 17, No. 77/78 (1961).
Takikawa et al., Chem Abs. 77, 101080 (1972).
Rapporport ed. "Chemistry of the Cyano Group", 1970, pp. 274–275.
T. L. Cairns et al., Chem. Abs. 48, 6954f, (1954).
Girgis et al., Chem. Abs. 81, 152244t, (1974).
Takikawa et al., Chem. Abs. 77, 18874n, (1972).

*Primary Examiner*—Raymond V. Rush
*Assistant Examiner*—Mark L. Berch

[57] ABSTRACT

Compounds of the formula

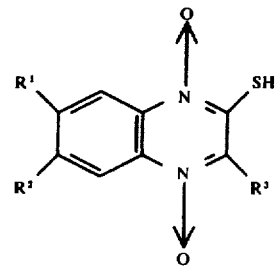

and alkali metal or alkaline earth metal salts thereof, wherein $R^1$ and $R^2$ are the same or different and each is hydrogen, alkyl, alkoxy, haloalkyl, polyhaloalkyl, haloalkoxy, polyhaloalkoxy or halo; $R^3$ is methyl, hydroxy or amino; are produced by treating the corresponding 3-cyanoquinoxaline-di-N-oxide of the formula

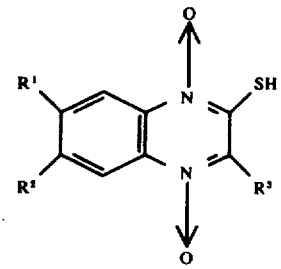

wherein $R^1$, $R^2$ and $R^3$ are as above defined, with hydrogen sulfide or an alkali metal or alkaline earth metal salt thereof. When a salt of hydrogen sulfide is used, the resulting mercaptide product may be converted to the corresponding mercaptan by treatment with an acid to produce the corresponding 2-mercaptoquinoxaline-di-N-oxide.

20 Claims, No Drawings

2-MERCAPTOQUINOXALINE-DI-N-OXIDE PRODUCTS AND A METHOD FOR THEIR PREPARATION

This is a division of Ser. No. 491,226 filed July 24, 1974, now abandoned.

This invention relates to a new class of 2--mercaptoquinoxaline-di-N-oxide products and to a novel method for their preparation. The said products have utility as intermediates in the synthesis of pharmaceuticals and also exhibit antimicrobial properties.

The products of this invention are 1-mercaptoquinoxaline-di-N-oxides of the following formula:

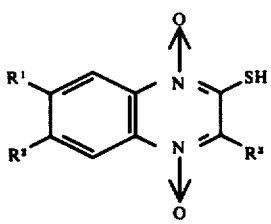

wherein
$R^1$ and $R^2$ are the same or different members selected from hydrogen; alkyl, for example, straight or branched chain lower alkyl of 1 to 6 carbon atoms, and preferably lower alkyl of 1 to 4 carbon atoms, such as methyl, ethyl, n-propyl, n-butyl, isobutyl and tertiary butyl; alkoxy, for example, straight or branched chain lower alkoxy of 1 to 6 carbon atoms, and preferably lower alkoxy of 1 to 4 carbon atoms, such as methoxy, ethoxy, n-propoxy, isopropoxy, n-butoxy, isobutoxy and tertiary butoxy; haloalkyl, for example, halo lower alkyl of 1 to 6 carbon atoms, preferably halo lower alkyl of 1 to 4 carbon atoms, and most preferably, halo lower alkyl of 1 or 2 carbon atoms, such as bromomethyl and 2-chloro-ethyl and the like; polyhaloalkyl, for example, polyhalo lower alkyl of 1 to 6 carbon atoms, preferably, polyhalo lower alkyl of 1 to 4 carbon atoms, and most preferably, 1 or 2 carbon atoms in which the polyhalo lower alkyl group contains from 2 to 5 halo atoms, as, for example, trifluoromethyl, chloro-difluoromethyl, 2,2,2,-trifluoroethyl and pentafluoroethyl and the like; halo alkoxy, for example, halo lower alkoxy of 1 to 6 carbon atoms, preferably 1 or 2 carbon atoms, as, for example, chloromethoxy, 2-chloroethoxy, 3-chloropropoxy, 4-bromobutoxy or 2-fluoroethoxy and the like; polyhaloalkoxy, for example, polyhalo lower alkoxy of 1 to 6 carbon atoms, preferably, polyhalo lower alkoxy of 1 to 4 carbon atoms, and most preferable 1 or 2 carbon atoms, as, for example, trifluoromethoxy or 2,2,2-trifluorethoxy and the like; or halo, for example, chloro, bromo or fluoro, preferably, chloro or fluoro; and $R_3$ is methyl, hydroxy or amino;

and the alkali metal and alkaline earth metal salts thereof as, for example, the sodium, potassium and calcium salts.

In this invention it is to be understood that the term "salts" includes both the alkali metal and alkaline earth metal salts of the thio moiety at position 2 and the alkali metal and alkaline earth metal salts of the hydroxy, moiety at position 3 when $R^3$ in formula I is hydroxy.

A preferred embodiment of this invention comprises those 2-mercaptoquinoxaline-di-N-oxide products (I) wherein $R_1$ and $R_2$ are the same or different members selected from hudrogen, lower alkyl, lower alkoxy, especially lower alkyl and lower alkoxy of 1 to 4 carbon atoms or chloro, fluoro or trifluoromethyl, and $R_3$ is methyl, hydroxy or amino; and the alkali metal and alkaline earth metal salts thereof.

An especially preferred embodiment of this invention comprises those 2-mercapto-quinoxaline-di-N-oxide products (I) wherein $R_1$ and $R_2$ are the same or different members selected from hydrogen, methyl, methoxy, ethoxy, fluoro, chloro or trifluoromethyl and $R_3$ is methyl, hydroxy or amino; and the alkali metal and alkaline earth metal salts thereof.

The preferred alkali metal and alkaline earth metal salts of the instant products (I) are the sodium, potassium and calcium salts.

The 2-mercapto-quinoxaline-di-N-oxide products (I) of this invention are obtained by treating the corresponding 3-cyanoquinoxaline-di-N-oxide precursor (II, infra) with hydrogen sulfide or with an alkali metal or alkaline earth metal salt thereof. When a salt of hydrogen sulfide is used, the resulting product is a mercaptide formed at position 2 of the quinoxaline-di-N-oxide nucleus (I). Said mercaptide may be converted to the corresponding mercaptan by treatment with an acid to afford the corresponding 2-mercapto-quinoxaline-di-N-oxide (I). The following equation, wherein the reagent employed is the sodium salt of hydrogen sulfide illustrates the process of this invention; however, it is to be understood that either hydrogen sulfide or any other alkali metal or alkaline earth metal salt of hydrogen sulfide may be substituted therefor in an otherwise similar process to afford an identical product:

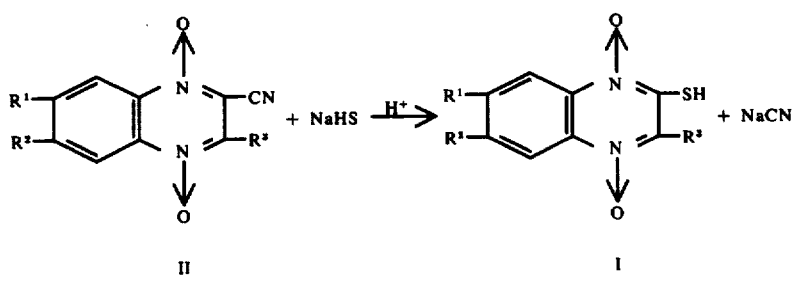

wherein $R^1$, $R^2$ and $R^3$ are as above defined.

Diluents which can be used in this process include water and all inert organic solvents. Preferred organic diluents are polar organic diluents, for example alcohols, especially alkanols having 1 to 4 carbon atoms, as, for example, methanol, ethanol, propanol and butanol, or nitriles, especially alkyl nitriles containing from 2 to 4 carbon atoms, as, for example, acetonitrile and propionitrile, or dialkylformamides containing 1 to 3 carbon atoms per alkyl group such as dimethylformamide.

Water is particularly advantageous as a diluent. The said diluents, including water, can be employed individually or in any desired combination with one another.

The reaction is carried out at a temperature between 0° and 150° C, preferably between 20 and 40° C. The reaction can be carried out under normal pressure but also under elevated pressure. In general, it is carried out under normal pressure.

Hydrogen sulphide can be employed as a gas or in the dissolved form, for example as an aqueous solution. The hydrogen sulphide is advantageously used in the form of one of its alkali metal salts, especially sodium and potassium salts, or alkaline earth metal salts, especially its calcium salts. Sodium sulphide, sodium hydrogen sulphide, potassium sulphide, potassium hydrogen sulphide and calcium sulphide may be mentioned as examples of suitable salts of hydrogen sulphide.

In carrying out the process according to this invention, preferably at least 1 mol of hydrogen sulphide or a corresponding amount of an alkali metal of alkaline earth metal salt of hydrogen sulphide is employed per 1 mol of cyano compound of the general formula II. If salts of hydrogen sulphide are used, the quinoxaline-di-N-oxide-mercaptides are obtained, and these can, if desired, be converted into the corresponding free mercapto compounds by acidification.

However, the molar ratio can be varied over a wide range without a particularly adverse effect on the process according to this invention.

The conversion of the mercaptide salts to their corresponding mercaptan products can be accomplished by known means, and, in principle it is possible to use any non-oxidizing organic or inorganic acid. Suitable organic acids include, for example, carboxylic acids, especially formic, acetic, propionic, butyric, citric, tartaric and benzoic acids may be mentioned, and, as examples of suitable inorganic acids, hydrogen halide acids, for example hydrochloric and hydrobromic acids, sulphuric acid and phosphoric acid, may be mentioned.

The instant products (I) can be isolated by generally customary methods, as for exqmple, by filtration and, if desired, can be purified by conventional means as, for example, by recrystallisation.

The mercapto compounds of formula I can be converted into alkali metal or alkaline earth metal salts by conventional means, preferably, by reacting them with alkali metal or akaline earth metal hydroxides as, for example, sodium or calcium hydroxide, or alkali metal or alkaline earth metal bicarbonates such as potassium bicarbonate, or alkali metal or alkaline earth metal carbonates such as sodium or calcium carbonate, or with the oxides of said metals.

If mixtures of the starting cyano-compounds of the general formula II are employed, in which $R^1$ and $R^2$ are different, corresponding mixtures of the compounds of the invention are obtained in the process according to the invention. These mixtures can be separated by generally customary methods of separation, for example paper chromatography, thin layer chromatography or column chromatography.

It is well known that nitriles react with hydrogen sulfide and salts of hydrogen sulfide to afford the corresponding thioamides. It is surprising, therefore, that in the instant process the 2-cyano-quinoxaline-di-N-oxide reactants (II) react with the hydrogen sulfide and sodium hydrogen sulfide to afford the corresponding 2-mercaptol-quinoxaline-di-N-oxide products, because, on the basis of the prior art it would have been expected that the corresponding 2-thioamido-quinoxaline-di-N-oxide would be obtained. In this regard, attention is directed to the following reference: Houben Weyl "Methoden der Organischen Chemie", Volume VIII, page 346, Georg Thieme Verlag, Stuttgart, 1952.

The starting compounds of the general formula II in which $kR^3$ represents hydroxyl can be prepared by dissolving about 1 mol of an appropriately substituted benzofuroxane in an organic solvent, for example in 300 ml of dimethylformamide, and adding about 1 mol of a cyanoacetic acid lower alkyl ester, for example cyanoacetic acid methyl ester, and a small (catalytic) amount of a base, for example diazobicyclononene. An exothermic reaction starts, whereupon the mixture is preferably cooled slighty. The resulting end product of the general formula II, in which $R^3$ represents hydroxyl, precipitates and is isolated according to customary methods and purified if desired.

The 2-cyano-3-amino-quinoxaline-di-N-oxide starting materials (II) are prepared by dissolving approximately 1 mol of an appropriately substituted benzofuroxane in a suitable organic solvent such as dimethylformamide followed by the addition of an approximately equivalent amount of malonic acid dinitrile and a small amount of a base such as triethylamine to function as a catalyst. An exothermic reaction commences whereupon it is preferable to cool the mixture slightly. The resulting 2-cyano-3-amino-quinoxaline-di-N-oxide precipitates and is isolated and purified by conventional means. The following equation illustrates this method of preparation.

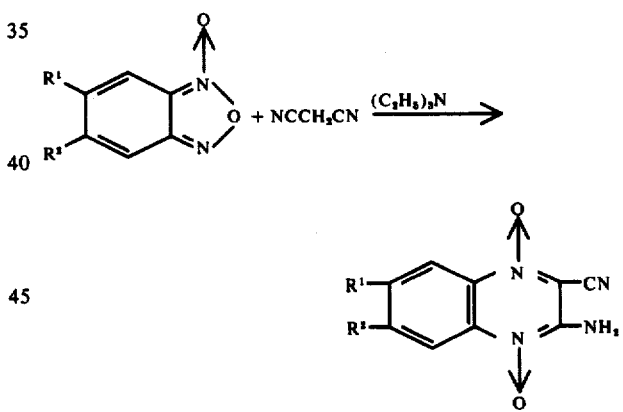

wherein $R^1$ and $R^2$ as defined above.

The 2-cyano-3-methyl-quinoxaline-di-N-oxide starting materials (II) are prepared by dissolving or suspending approximately 1 mol of an appropriately substituted benzofuroxane in a watermiscible solvent as, for example, in methanol, followed by the addition of approximately 1 mol of ammonium chloride and 2 to 3 mols of ammonia. The reaction mixture is maintained at a temperature of about 20° to 30° C. A solution of 5-methyl-isoxazole in methanol, which has previously been heated with a solution of an alkali metal hydroxide, preferably potassium hydroxide, at a temperature of between about 40° and about 80° C for about 1 to about 60 minutes, is added dropwise to the mixture at about 20° to 80° C. An exothermic reaction occurs which may require occasional cooling, whereupon, the desired 2-cyano-3-amino-quinoxaline-di-N-oxide compound precipitates and is then isolated and purified by conventional means. The following equation illustrates this method of preparation.

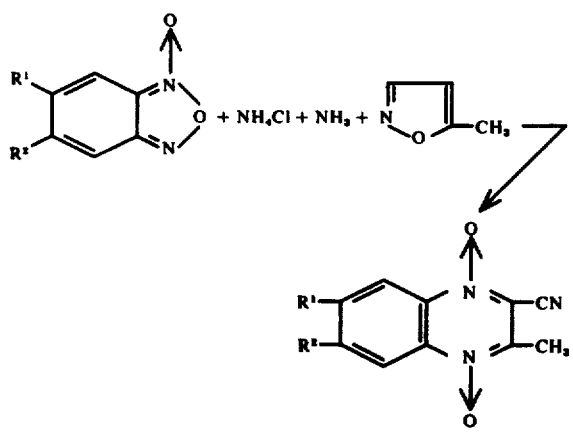

wherein $R^1$ and $R^2$ are as defined above.

The following compounds illustrate the starting materials (II) which are utilized in the process of this invention. The designation "6(7)" which appears in the following list of compounds and throughout this specification is intended to indicate that the compounds thus described are a mixture of compounds substituted respectively in the 6-and7-positions of the quinoxaline-de-N-oxide nucleus:

2-methyl-3-cyano-quinoxaline-di-N-oxide,
2-hydroxy-3-cyano-quinoxaline-di-N-oxide,
2-amino-3-cyano-quinoxaline-di-N-oxide,
6-(7-)methyl-2methyl-3-cyano-quinoxaline-di-N-oxide,
6-(7-)ethyl-2-methyl-3-cyano-quinoxaline-di-N-oxide,
6-(7-)methoxy-2-methyl-3-cyano-quinoxaline-di-N-oxide,
6-(7-)ethoxy-2-methyl-3-cyano-quinoxaline-di-N-oxide,
6-(7-)methoxyethyl-2-amino-3cyano-quinoxaline-di-N-oxide,
6-(7-)fluoromethyl-2-amino-3-cyano-quinoxaline-di-N-oxide,
6-(7-)chloromethoxy-2-amino-3-cyano-quinoxaline-di-N-oxide,
6-(7-)n.-propoxy-2amino-3-cyano-quinoxaline-di-N-oxide,
6l(7-)trifluoromethyl-2-amino-3-cyano-quinoxaline-di-N-oxide,
6-(7-)chloro-difluoromethyl-2-amino-3cyano-quinoxaline-di-M-oxide,
6-(7-)chloro-2-amino-3-cyano-quinoxaline-di-N-oxide,
6-(7-)fluro-2-hydroxy-3cyano-quinoxaline-di-N-oxide,
6-(7-)bromo-2-hydroxy-3-cyano-quinoxaline-di-N-oxide,
6,7-dimethyl-2-hydroxy-3-cyano-quinoxaline-di-N-oxide,
6,7-diethyl-2-hydroxy-3-cyano-quinoxaline-di-N-oxide,
6,7-dimethoxy-2-hydroxy-3-cyano-quinoxaline-di-N-oxide,
6,7-diethoxy-2-hydroxy-3-cyano-quinoxaline-di-N-oxide,
6,7-dichloro-2-hydroxy-3-cyano-quinoxaline-di-N-oxide,
6,7-dibromo-2-hydroxy-3-cyano-quinoxaline-di-N-oxide,
6,7-difluoro-2-hydroxy-3-cyano-quinoxaline-di-N-oxide and
6-methyl-7-chloro-2-hydroxy-3-cyano-quinoxaline-di-N-oxide.
7-methyl-6-chloro-2-hydroxy-3-cyano-quinoxaline-di-N-oxide The 2-mercapto-quinoxaline-di-N-oxide products of this invention have utility as intermediates in the preparation of the antibacterially active thio- and sulphonyl-quinoxaline-di-N-oxides described in British Pat. No. 1,293,850. According to this procedure, the instant products (I) are alkylated by conventional means as, for example, by treatment with alkylhalide such as methyliodide or, preferably, by treatment with the dialkylsulphates such as dimethylsulphate at temperatures from 20° to 30° C in an aqueous alkaline solution such as aqueous solution of sodium hydroxide. The alkylated products thus obtained can be isolated by filtration extraction according to conventional means and then purified for use as antibacterial agents.

In addition to their use as intermediates, the instant products (I) exhibit an antimicrobial effect. They exhibit a broad antibacterial activity which is effective against both Gram-positive and Gram-negative microbes. The instant products, therefore, can be formulated according to conventional means which are well known in the art for use as disinfectants or prophylactics of the most diverse kind as, for example, in use with platics, lubricants, fabrics and the like. The choice of suitable concentrations and excipients for formulating the compositions which use the instant products as the active ingredients is within the skill of the artisans to determine.

The antimicrobial activity of the instant products (I) is demonstrated by the following in vitro experiments. The minimum inhibitory concentrations were tested by means of the plate test and the composition of the nutrient medium utilized is as follows:

| | |
|---|---|
| Proteose peptone | 10 g |
| Veal extract | 10 g |
| Dextrose | 2 g |
| Sodium chloride | 3 g |
| Disodium phosphate | 2 g |
| Na Acetate | 1 g |
| Adenine sulphate | 0.01 g |
| Guanine hydrochloride | 0.01 g |
| Uracil | 0.01 g |
| Xanthine | 0.01 g |
| Agar | 12 g |
| pH 7.4 | |
| Distilled water | 1,000 ml |

The bacteria to be tested are cast, together with the nutrient medium and the test substance distributed in the agar, into a Petri dish. The number of bacterial cells is 5,000/10 ml of nutrient medium. The minimum inhibitory concentration is the concentration at which 0–10 colonies are formed.

Table A

| Compound from Example No. | Minimum inhibitory concentration in γ/ml of nutrient medium | | | | |
|---|---|---|---|---|---|
| | *Escherichia coli* A 261 | *Escherichia coli* C 165 | *Proteus vulgaris* 1017 | *Klebsiella* 8085 | *Staphylococcus aureus* 133 |
| 1 | 50–100 | 50–100 | 100 | 10 | 100 |
| 2 | 128 | 128 | 64–128 | 128 | 128 |
| 3 | 128 | 64–128 | 128 | — | 128 |
| 4 | 100 | 100 | — | — | 100 |
| 7 | 128 | 64–128 | 128 | — | 128 |

The 2-mercaptoquinoxaline-di-N-oxides (I) of this invention are conveniently employed in antibacterial formulations, such as solutions, emulsions, suspensions, powders, pastes and granulates. These can be produced in the usual manner, as for example by mixing the 2-mercaptoquinoxaline-di-N oxide with extenders, that is liquid, solid or liquefied gaseous diluents or carriers, optionally with the use of surface-active agents, such as emulsifying agents or dispersing agents.

Suitable emulsifying agents include nonionic and anionic emulsifiers such as polyoxyethylene-fatty acid esters, polyoxyethylene-fatty alcohol ethers for example alkylarylpolyglycol ethers, alkyl sulfonates, alkyl sulfates and aryl sulfonates. Dispersing agents include lignin, sulfite waste liquors and methyl cellulose.

The compositions can be used for disinfectant purposes as, for example, in the disinfection of equipment used in the production, handling or storage of food or drink. In addition, they are suitable for disinfecting medical instruments and equipment.

The compositions may be used in accordance with generally customary methods as, for example, by immersing the object to be disinfected into a solution of the composition or by applying the composition to the said object.

The compositions generally contain 0.1 to 95% by weight of the 2-mercaptoquinoxaline-di-N-oxide (I), in a form ready for use or appropriately diluted prior to actual application. Other auxiliaries or active substances, such as disinfectants or antibacterial agents can also be admixed with the said formulations or ready-to-use solutions.

The 2-mercaptoquinoxaline-di-N-oxide (I) is used either in the form of a pure compound or as a composition containing the said pure compound in the usual manner, as for example by powdering, spraying, watering, as an aerosol or as a dip. When used as an aerosol, the composition may contain the usual propellant such as an halogenated hydrocarbon, for example, freon.

This invention therefore provides an antibacterial composition containing as the active ingredient a 2-mercaptoquinoxaline-di-N-oxide (I) in admixture with a solid or liquefied gaseous diluent or carrier or in admixture with a liquid diluent or carrier containing a surface-active agent.

The following examples are presented by way of illustration and not by way of limitation.

Example 1:
2-Mercapto-3-methylquinoxaline-di-N-oxide

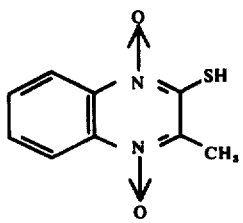

Step A: 2-Cyano-3-methyl-quinoxaline-di-N-oxide

Benzofuroxane (492 g., 3.62 mols) is suspended in methoanol (1,000 ml), ammonium chloride (204 g., 3.8 mols) is added and ammonia (2 to 3 mols) is introduced at 20° to 30° C. A solution of 393 g of an isomeric mixture of 70% by weight of 5-methylisooxazole and 30% by weight of 4-methylisoxazole (corresponding to 3.31 mols of 5-methylisoxazole) in 250 ml of methanol (which has been heated beforehand for 30 minutes with a solution of potassium hydroxide (186 g., 3.31 mols) in 1.5 liters of methanol to 50° C) is added dropwise, without application of heat, to the above suspension, under stirring and while ammonia is passed slowly into the mixture.

Upon addition of the benzofuroxane, the temperature of the mixture rises to 45° C. After the exothermic effect has subsided, the mixture is warmed to 40°–45° C for an additional 4 hours. During the reaction the benzofuroxane dissolves and the reaction product separates out in the form of yellow crystals. The said crystalline product is filtered off, washed with water and methanol and dried to afford 572 g (86% of theory based upon the amount of 5-methylisoxazole utilized) of 2-cyanol-3-methyl-quinoxaline-di-N-oxide-(1,4) in the form of yellow crystals. After recrystallisation from acetonitrile melt, the said product decomposes at 194° C.

Step B: 2-Mercapto-3-methyl-quinoxaline-di-N-oxide

2-Cyano-3-methyl-quinoxaline-di-N-oxide (201 g., 1 mol) is suspended in water (400 ml) and a solution of sodium sulfide nonahydrate, i.e. $1Na_2S.9 H_2O$ (240 g., 1.0 mol) in water (400 ml) is added dropwise. An exothermic reaction results and a yellow-brown precipitate separates out. The filtrate is then filtered off after one hour and dissolved in water. Upon acidification with acetic acid, 2-mercapto-3-methyl-quinoxaline-di-N-oxide (183 g., 88% of theory) precipitates in the form of yellow crystals which, after recrystallisation from acetonitrile melt, decomposes at 156°–158° C.

Analysis $C_9H_8N_2O_2S$ (208). Calculated: C 51.9 H 3.85 N 13.4 S 15.4. Found: C 51.8 H 3.6 N 13.4 S 15.2.

By following the procedure of Example 1, Steps A and B, all of the 2-mercapto-3-methyl-quinoxaline-di-N-oxide products of this invention may be obtained. Thus, for example, by substituting the appropriately substituted 5(6)-benzofuroxane starting material (III) for the benzofuroxane of Example 1, Step A, and following the procedure described therein, the corresponding 6(7)-2-cyano-3-methyl-quinoxaline-di-N-oxide intermediate (IIa, infra) is obtained; and, when said intermediate (IIa) is subjected to the mercaptylation reaction of Example 1, Step B, the corresponding 6(7)-substituted 2-mercaptol-3-methyl-quinoxaline-di-N-oxide product is obtained. The following equation illustrates the method of Example 1, Steps A and B, and, taken together with Table I, illustrate the starting materials employed therein and the intermediates and final products produced thereby:

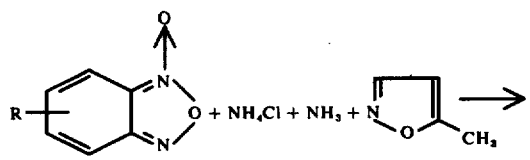

III

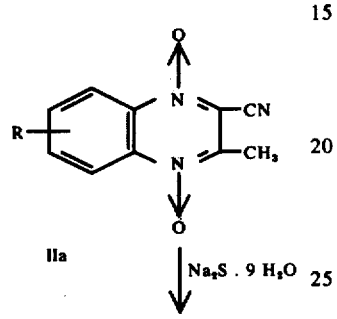

IIa

↓ Na₂S . 9 H₂O

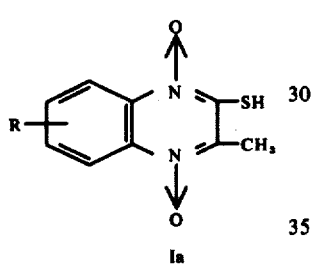

Ia

Table I

| Example | R | Product Ia |
|---|---|---|
| 2 | Cl | 6(7)-chloro-2-mercapto-3-methyl-quinoxaline-di-N-oxide |
| 3 | F | 6(7)-fluoro-2-mercapto-3-methyl-quinoxaline-di-N-oxide |
| 4 | Br | 6(7)-bromo-2-mercapto-3-methyl-quinoxaline-di-N-oxide |
| 5 | —CH₃ | 6(7)-methyl-2-mercapto-3-methyl-quinoxaline-di-N-oxide |
| 6 | —C₂H₅ | 6(7)-ethyl-2-mercapto-3-methyl-quinoxaline-di-N-oxide |
| 7 | —OCH₃ | 6(7)-methoxy-2-mercapto-3-methyl-quinoxaline-di-N-oxide |
| 8 | —OC₂H₅ | 6(7)-ethoxy-2-mercapto-3-methyl-quinoxaline-di-N-oxide |

Table I-continued

| Example | R | Product Ia |
|---|---|---|
| 9 | —CF₃ | 6(7)-trifluoromethyl-2-mercapto-3-methyl-quinoxaline-di-N-oxide |

In like manner, the 6,7-disubstituted 2-mercapto-3-methyl-quinoxaline-di-N-oxide products (Ib, infra) are obtained by substituting the appropriate 5,6-disubstituted benzofuroxane (IIIa, infra) for the benzofuroxane of Example 1, Step A, and otherwise following the procedure described in Steps A and B of said example. The following equation illustrates the method of Example 1, Steps A and B, and, in combination with Table II, depicts the starting materials employed in the said method and the final products obtained thereby:

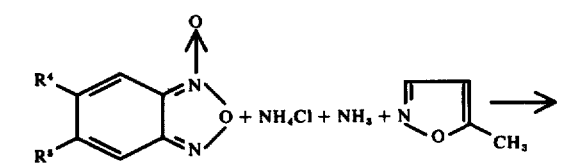

IIIa

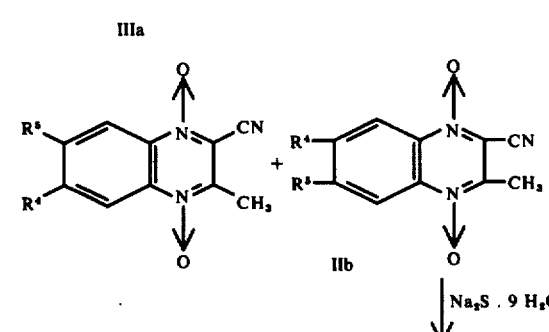

IIb

↓ Na₂S . 9 H₂O

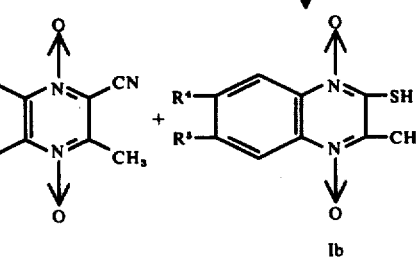

Ib

Table II

| Example | R⁴ | R⁵ | Product Ib |
|---|---|---|---|
| 10 | Cl | Cl | 6,7-dichloro-2-mercapto-3-methyl-quinoxaline-di-N-oxide |
| 11 | F | F | 6,7-difluoro-2-mercapto-3-methyl-quinoxaline-di-N-oxide |
| 12 | Br | Br | 6,7-dibromo-2-mercapto-3-methyl-quinoxaline-di-N-oxide |
| 13 | —CH₃ | —CH₃ | 6,7-dimethyl-2-mercapto-3-methyl-quinoxaline-di-N-oxide |
| 14 | —C₂H₅ | —C₂H₅ | 6,7-diethyl-2-mercapto-3-methyl-quinoxaline-di-N-oxide |
| 15 | —OCH₃ | —OCH₃ | 6,7-dimethoxy-2-mercapto-3-methyl-quinoxaline-di-N-oxide |
| 16 | —OC₂H₅ | —OC₂H₅ | 6,7-diethoxy-2-mercapto-3-methyl-quinoxaline-di-N-oxide |
| 17 | —CF₃ | —CF₃ | 6,7-di-trifluoromethyl-2-mercapto-3-methyl-quinoxaline-di-N-oxide |
| 18 | F/(Cl) | Cl/(F) | 6(7)-chloro-7(6)-fluoro-2-mercapto-3-methyl-quinoxaline-di-N-oxide |
| 19 | —CH₃/(Cl) | Cl/(CH₃) | 6(7)-chloro-7(6)-methyl-2-mercapto- |

Table II-continued

| Example | R⁴ | R⁵ | Product Ib |
|---|---|---|---|
| 20 | —OCH₃/(Cl) | Cl/OCH₃ | 3-methyl-quinoxaline-di-N-oxide<br>6(7)-chloro-7(6)-methoxy-2-mercapto-3-methyl-quinoxaline-di-N-oxide |

If R⁴ and R⁵ are different mixtures of the compounds of the following formulae are obtained.

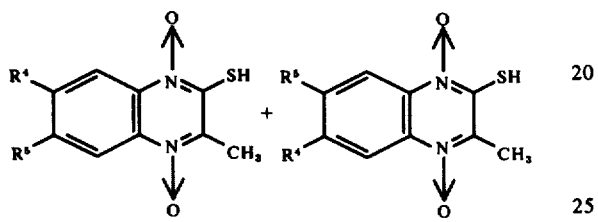

Example 21:
2-Mercapto-3-methyl-6(7)-chloroquinoxaline-di-N-oxide

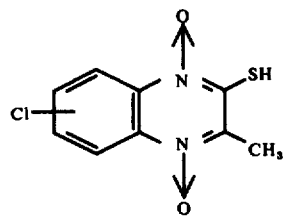

Upon substituting 6(7)-chloro-2-cyano-3-methyl-quinoxaline-di-N-oxide for the 2-cyano-3-methyl-quinoxaline-di-N-oxide of Example 1 (Step B) and following the procedure described therein, there is thus obtained a 1:1 mixture of 2-mercapto-3-methyl-6(7)-chloroquinoxaline-di-N-oxide having a decomposition point of 150° C.

EXAMPLE 22:
2-MERCAPTO-3-METHYL-6(7)-ETHOXY-QUINOXALINE-DI-N-OXIDE

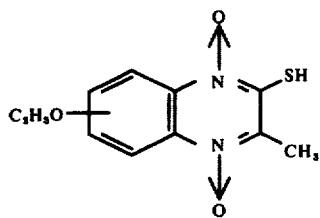

Upon substituting 6(7)-ethoxy-2-cyano-3-methyl-quinoxaline-di-N-oxide for the 2-cyano-3-methyl qui-noxaline-di-N-oxide of Example 1 (Step B) and following the procedure described therein, there is thus obtained an approximately 1:1 mixture of 2-mercapto-3-methyl-6(7)-ethoxy-quinoxaline-di-N-oxide having a decomposition point of 176° C.

EXAMPLE 23:
2-MERCAPTO-3-AMINOQUINOXALINE-DI-N-OXIDE

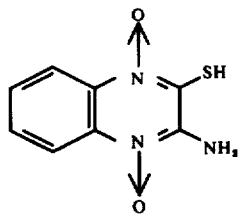

STEP A:
2-CYANO-3-AMINOQUINOXALINE-DI-N-OXIDE

Benzofuroxane (136 g., 1.0 mol) is dissolved in dimethylformamide (300 ml) and malonic acid dinitrile (66 g., 1.0 mol) and triethylamine (5.0 g) is added. The temperature is kept at 40°–50° C by cooling. 2-Cyano-3-amino-quinoxaline-di-N-oxide precipitates and is filtered off and recrystallised, melting point: 232° C (decomposition).

STEP B:
2-MERCAPTO-3-AMINIOQUINOXALINE-DI-N-OXIDE

2-Cyano-3-amino-quinoxaline-di-N-oxide (20.2 g., 0.1 mol) is suspended in water (50 ml) and 100 g of an 18.5% aqueous sodium hydrogen sulphide solution is added dropwise. An exothermic reaction commences and the suspension turns dark blue. After about 2 hours, a red-brown solution has been produced. When the solution is acidified with dilute hydrochloric acid, 19 g (91% of theory) of yellow-green crystals of 2-mercapto-3-amino-quinoxaline-di-N-oxide separate out. After boiling with methanol the crystalline product melts with decomposition at 185° C.

Analysis $C_8H_7N_3O_2S$ (209).

Calculated: C 46.0 H 3.55 N 20.1 S 15.3.

Found: C 46.2 H 3.1 N 20.2 S 15.0.

By substituting the appropriate starting materials for those described in Example 23, Steps A and B, and otherwise following the procedure described therein, all of the 2-mercapto-3-amino-quinoxaline-di-N-oxide products of this invention may be obtained. Thus, for example, by substituting the appropriate 5(6)-monosubstituted benzofuroxane starting material (IIIb, infra) for the benzofuroxane starting material of Example 23, Step A, and following the procedure described therein, the corresponding 6(7)-monosubstituted 2-cyano-3-amono-quinoxaline-di-N-oxide intermediate (IIc, infra) is obtained; and, when said intermediate (IIc) is treated with an aqueous sodium hydrogen sulfide solution, according to the procedure described in Example 23, Step B, the corresponding 6(7)-monosubstituted 2-mercapto-3-amino-quinoxaline-di-N-oxide product (Ic, infra) is obtained. The following equation illustrates the method of Example 23, Steps A and B, and, taken together with Table III, depicts the starting materials and final products obtained thereby:

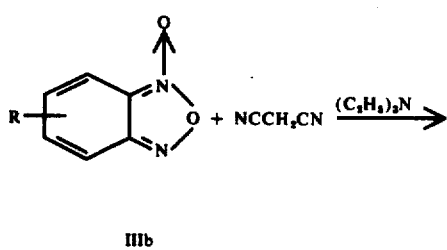

IIIb

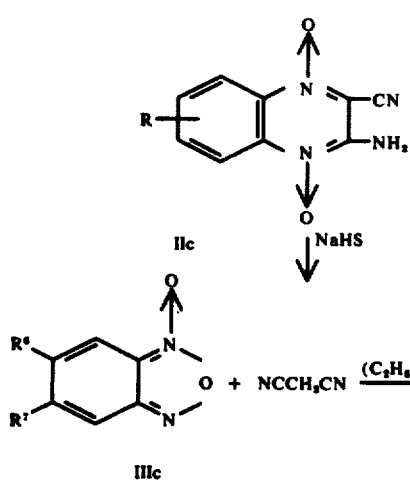

Ic

Table III

| Example | R | Product Ic |
|---|---|---|
| 24 | F | 6(7)-fluoro-2-mercapto-3-amino-quinoxaline-di-N-oxide |
| 25 | Br | 6(7)-bromo-2-mercapto-3-amino-quinoxaline-di-N-oxide |
| 26 | —C$_2$H$_5$ | 6(7)-ethyl-2-mercapto-3-amino-quinoxaline-di-N-oxide |
| 27 | —OCH$_3$ | 6(7)-methoxy-2-mercapto-3-amino-quinoxaline-di-N-oxide |
| 28 | —OC$_2$H$_5$ | 6(7)-ethoxy-2-mercapto-3-amino-quinoxaline-di-N-oxide |
| 29 | —CF$_3$ | 6(7)-trifluoromethyl-2-mercapto-3-amino-quinoxaline-di-N-oxide |

In like manner, the 6,7-disubstituted 2-mercapto-3-amino-quinoxaline-di-N-oxide products (Id, infra) are obtained by substituting the appropriate 5,6-disubstituted benzofuroxane (IIIc) for the benzofuroxane of Example 23, Step A, and otherwise following the procedure described in Steps A and B of said example. The following equation illustrates this method and, taken together with Table IV, depicts the starting materials employed in the said process and the products obtained thereby:

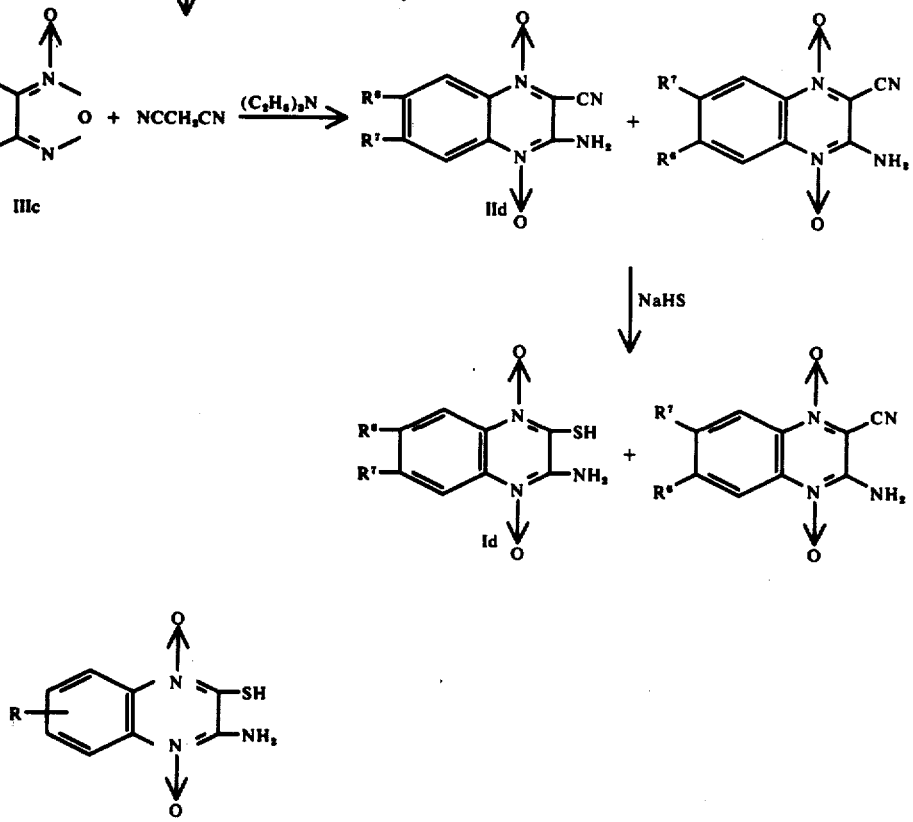

Table IV

| Example | R$^6$ | R$^7$ | Product Id |
|---|---|---|---|
| 30 | Cl | Cl | 6,7-dichloro-2-mercapto-3-amino-quinoxaline-di-N-oxide |
| 31 | F | F | 6,7-difluoro-2-mercapto-3-amino-quinoxaline-di-N-oxide |
| 32 | Br | Br | 6,7-dibromo-2-mercapto-3-amino-quinoxaline-di-N-oxide |
| 33 | —CH$_3$ | —CH$_3$ | 6,7-dimethyl-2-mercapto-3-amino-quinoxaline-di-N-oxide |
| 34 | —C$_2$H$_5$ | —C$_2$H$_5$ | 6,7-diethyl-2-mercapto-3-amino-quinoxaline-di-N-oxide |
| 35 | —OCH$_3$ | —OCH$_3$ | 6,7-dimethoxy-2-mercapto-3-amino-quinoxaline-di-N-oxide |
| 36 | —OC$_2$H$_5$ | —OC$_2$H$_5$ | 6,7-diethoxy-2-mercapto-3-amino-quinoxaline-di-N-oxide |
| 37 | —CF$_3$ | —CF$_3$ | 6,7-di-trifluoromethyl-2-mercapto-3-amino-quinoxaline-di-N-oxide |
| 38/39 | Cl/(F) | F/(Cl) | 6-chloro-7-fluoro-2-mercapto-3- |

Table IV-continued

| Example | R⁶ | R⁷ | Product Id |
|---|---|---|---|
|  |  |  | amino-quinoxaline-di-N-oxide |
|  |  |  | 6-fluoro-7-chloro-2-mercapto-3- |
|  |  |  | amino-quinoxaline-di-N-oxide |
| 40 | Cl(CH₃) | —CH₃(Cl) | 6(7)-chloro-7(6)-methyl-2-mercapto- |
|  |  |  | 3-amino-quinoxaline-di-N-oxide |
| 41 | —OCH₃/(CH₃) | —CH₃/ (OCH₃) | 6(7)-methoxy-7(6)-methyl-2-mercapto- 3-amino-quinoxaline-di-N-oxide |

If R⁶ and R⁷ are different mixtures of the compounds of the following formulae are obtained:

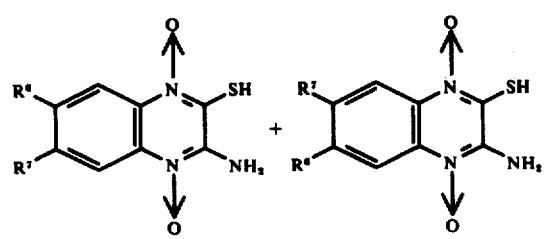

EXAMPLE 42:
2-MERCAPTO-3AMINO-6(7)-CHLORO-QUINOXALINE-DI-N-OXIDE

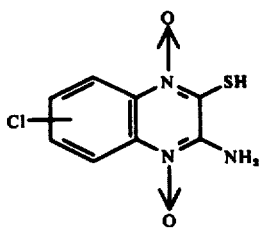

STEP A:
2-CYANO-3-AMINO-6(7)-CHLORO-QUINOXALINE-DI-N-OXIDE

Upon substituting an equivalent amount of 6(7)-chlorobenzofuroxane for the benzofuroxane of Example 23, Step A, and otherwise following the procedure described therein, there is thus obtained a mixture of the 6-chloro and 7-chloro isomers of 2-cyano-3-amino-quinoxaline-di-N-oxide, i.e., 2-cyano3-amino-6(7)-chloroquinoxaline-di-N-oxide.

STEP B:
2-MERCAPTO-3-AMINO-6(7)-CHLORO-QUINOXALINE-DI-N-OXIDE

Upon substituting an equivalent amount of 2-cyano-3-amino-6(7)-chloro-quinoxaline-di-N-oxide for the 2-cyano-3-aminoquinoxaline-di-N-oxide of Example 23, Step B, and otherwise following the procedure described therein, there is thus obtained an approximately 1:1 mixture of the 6-chloro and 7-chloro isomers of 3-amino-2-mercapto-quinoxaline-di-N-oxide, i.e., 2-mercapto-3-amino6(7)-chloro-quinoxaline-di-N-oxide, decomposition point 187° C.

EXAMPLE 43:
2-MERCAPTO-3-AMINO-6(7)-METHYL-QUINOXALINE-DI-N-OXIDE

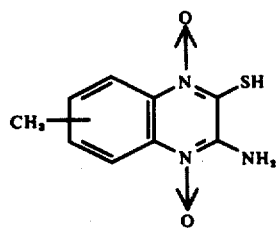

STEP A:
2-CYANO-3-AMINO-6(7)-METHYL-QUINOXALINE-DI-N-OXIDE

Upon substituting an equivalent amount of 6(7)-methyl-benzofuroxane for the benzofuroxane of Example 23, Step A, and otherwise following the procedure described therein, there is thus obtained a mixture of the 6-methyl and 7-methyl isomers of 2-cyano-3-amino-quinoxaline-di-N-oxide, i.e., 2-cyano-3-amino-6(7)-methylquinoxaline-di-N-oxide.

STEP B:
2-MERCAPTO-3-AMINO-6(7)-METHYL-QUINOXALINE-DI-N-OXIDE

Upon substituting an equivalent amount of 2-cyano-3-amino-6(7)-methyl-quinoxaline-di-N-oxide for the 2-cyano-3-aminoquinoxaline-di-N-oxide of Example 23, Step B, and otherwise following the procedure described therein, there is thus obtained an approximately 1:1 mixture of the 6-methyl and 7-methyl isomers of 2-mercapto-3-amino-quinoxaline-di-N-oxide, i.e., 2-mercapto-3-amino-6(7)-methyll-quinoxaline-di-N-oxide, decomposition point 193° C.

EXAMPLE 44:
2-MERCAPTO-3-HYDROXY-QUINOXALINE-DI-N-OXIDE

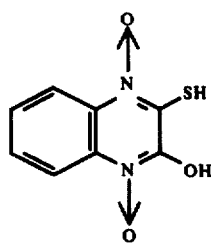

STEP A:
2-CYANO-3-HYDROXY-QUINOXALINE-DI-N-OXIDE

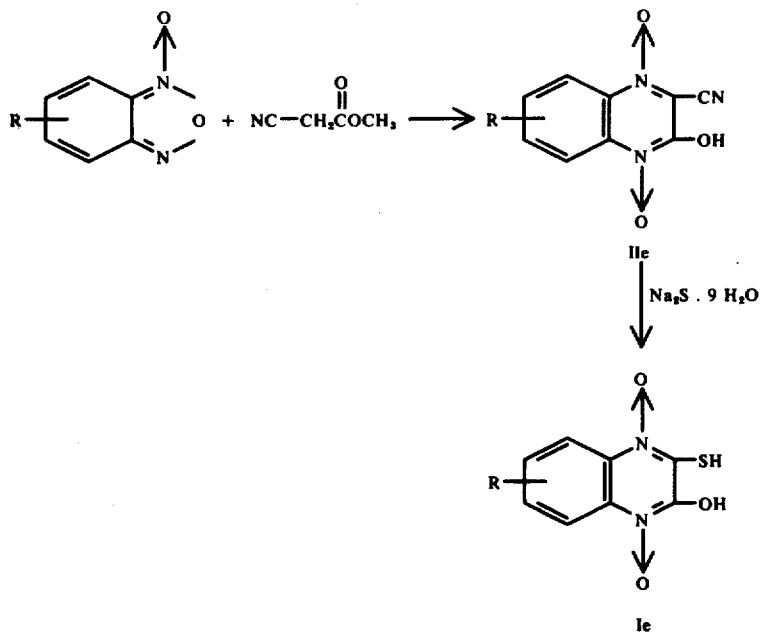

Benzofuroxane (136 g., 1.0 mol) is dissolved in dimethylformamide (300 ml) and cyanoacetic acid methyl ester (99 g., 1.0 mol) diazabicyclononene (10 g) is added. The temperature is kept at 40°–50° C by cooling. 2-Cyano-3hydroxy-quinoxaline-di-N-oxide precipitates and is filtered off and recrystallized, melting point: 226°–228° C (decomposition).

STEP B:
2-MERCAPTO-3-HYDROXY-QUINOXALINE-DI-N-OXIDE

2-Cyanol-3-hydroxy-quinoxaline-di-N-oxide (20.3 g., 0.1 mol) is suspended in water (300 ml) and sodium sulfide nonahydrate, i.e., $Na_2S.9\,H_2O$ (48 g., 0.2 mol) is added, whereupon a thick red precipitate separates out from the yellow suspension, and then redissolves after standing. When this solution is acidified with 10% strength aqueous hydrochloric acid, 20 g (95% of theory) of 2-mercapto-3-hydroxyl-quinoxaline-di-N-oxide precipitates out. After boiling in methanol, the said product melts with decomposition at 168° C.

Analysis $C_8H_6N_2O_3S$ (210).

Calculated: C 45.7 H 2.9 N 13.3 S 15.2.

Found: C 46.2 H 3.0 N 13.4 S 15.1.

Following the procedure of Example 44, Steps A and B, all of the 6(7)-monosubstituted 2-mercapto-3-hydroxy-quinoxaline-di-N-oxide products may be obtained. Thus, for example, by substituting the appropriate 5(6)-monosubstituted benzofuroxane starting material for the benzofuroxane of Example 44, Step A, and following the procedure described therein, the corresponding 2-cyano-3-hydroxy-6(7)-monosubstituted quinoxaline-di-N-oxide intermediate (IIe, infra) is obtained; and, when said intermediate (IIe) is subjected to the mercaptylation reaction of Example 44, Step B, the corresponding 6(7)-monosubstituted 2-mercapto-3-hydroxy-quinoxaline-di-N-oxide product (Ie, infra) is obtained. The following equation illustrates the method of Example 44, Steps A and B and, taken together with Table V, depicts the starting materials, intermediates and final products obtained thereby:

Table V

| Example | R | Product Ie |
|---|---|---|
| 45 | Cl | 6(7)-chloro-2-mercapto-3-hydroxy-quinoxaline-di-N-oxide |
| 46 | F | 6(7)-fluoro-2-mercapto-3-hydroxy-quinoxaline-di-N-oxide |
| 47 | Br | 6(7)-bromo-2-mercapto-3-hydroxy-quinoxaline-di-N-oxide |
| 48 | —CH₃ | 6(7)-methyl-2-mercapto-3-hydroxy-quinoxaline-di-N-oxide |
| 49 | —C₂H₅ | 6(7)-ethyl-2-mercapto-3-hydroxy-quinoxaline-di-N-oxide |
| 50 | —OCH₃ | 6(7)-methoxy-2-mercapto-3-hydroxy-quinoxaline-di-N-oxide |
| 51 | —OC₂H₅ | 6(7)-ethoxy-2-mercapto-3-hydroxy-quinoxaline-di-N-oxide |
| 52 | —CF₃ | 6(7)-trifluoromethyl-2-mercapto-3-hydroxy-quinoxaline-di-N-oxide |

In like manner, the 6,7-disubstituted 2-mercapto-3-hydroxy-quinoxaline-di-N-oxide products of this invention may be obtained by substituting the appropriate 5,6-benzofuroxane for the benzofuroxane of Example 44, Step A and otherwise following the procedure in Steps A and B of said example. The following equation, together with Table VI, illustrate the 5,6-disubstituted benzofuroxane starting materials which may be employed according to this process, the 6,7-disubstituted 2-cyano-3-hydroxy-quinoxaline-di-N-oxide intermediates derived therefrom (IIf, infra) and the 6,7-disubstituted 2-mercapto-3hydroxy-quinoxaline-di-N-oxide products (If, infra) obtained thereby:

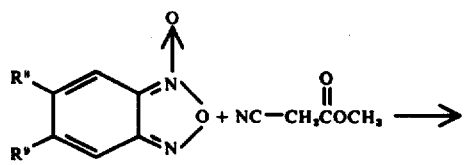

-continued

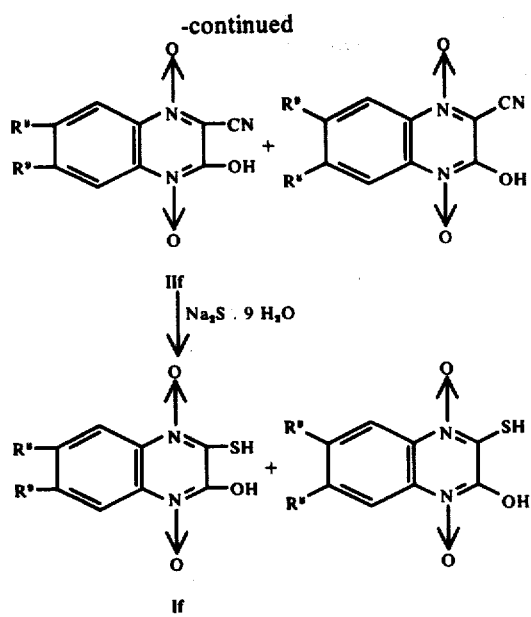

STEP A:
2-CYANO-3HYDROXY-6(7)-FLUORO-7(6)-CHLORO-QUINOXALINE-DI-N-OXIDE

Upon substituting an equivalent amount of 5-fluoro-6-chloro-benzofuroxane for the benzofuroxane of Example 44, Step A, and otherwise following the procedure described therein, there is thus obtained a mixture of 2-cyano-3-hydroxy-6-fluoro-l7-chloroquinoxaline-di-N-oxide and 2-cyano-3-hydroxy-6-chloro-7-fluoroquinoxaline-di-N-oxide, i.e. 2-cyano-3hydroxy-6(7)-fluoro-7(6)-chloro-quinoxaline-di-N-oxide.

STEP B:
2-MERCAPTO-3-HYDROXY-6(7)-FLUORO-7(6)-CHLOROQUINOXALINE-DI-N-OXIDE

Upon substituting an equivalent amount of 2-cyano-3-hydroxy-6(7)-fluoro-7(6)-chloro-quinoxaline-di-N-oxide for the 2-cyano-3-hydroxy-quinoxaline-di-N-oxide of Example 44, Step B, and otherwise following the procedure described therein, there is thus obtained an approximately 1:1 mixture of 2-mercapto-3-hydroxy-6-fluoro-7-chloro-quinoxaline-di-N-oxide and 2-mercapto-3-hydroxy-6-chloro-7-fluoro-quinoxaline- Table VI

| Example | R$^a$ | R$^b$ | Products If |
|---|---|---|---|
| 53 | Cl | Cl | 6,7-dichloro-2-mercapto-3-hydroxy-quinoxaline-di-N-oxide |
| 54 | F | F | 6,7-difluoro-2-mercapto-3-hydroxy-quinoxaline-di-N-oxide |
| 55 | Br | Br | 6,7-dibromo-2-mercapto-3-hydroxy-quinoxaline-di-N-oxide |
| 56 | —CH$_3$ | —CH$_3$ | 6,7-dimethyl-2-mercapto-3-hydroxy-quinoxaline-di-N-oxide |
| 57 | —C$_2$H$_5$ | —C$_2$H$_5$ | 6,7-diethyl-2-mercapto-3-hydroxy-quinoxaline-di-N-oxide |
| 58 | —OCH$_3$ | —OCH$_3$ | 6,7-dimethoxy-2-mercapto-3-hydroxy-quinoxaline-di-N-oxide |
| 59 | —OC$_2$H$_5$ | —OC$_2$H$_5$ | 6,7-diethoxy-2-mercapto-3-hydroxy-quinoxaline-di-N-oxide |
| 60 | —CF$_3$ | —CF$_3$ | 6,7-ditrifluoromethyl-2-mercapto-3-hydroxy-quinoxaline-di-N-oxide |
| 61/62 | F/(Cl) | Cl/(F) | 6-chloro-7-fluoro-2-mercapto-3-hydroxy-quinoxaline-di-N-oxide<br>6-fluoro-7-chloro-2-mercapto-3-hydroxy-quinoxaline-di-N-oxide |
| 63/64 | Cl/(CF$_3$) | —CF$_3$/(Cl) | 6-(7)-trifluoro-7(6)-chloro-2-mercapto-3-hydroxy-quinoxaline-di-N-oxide |
| 65 | —CH$_3$/(Cl) | Cl/(CH$_3$) | 6(7)-chloro-7(6)-methyl-2-mercapto-3-hydroxy-quinoxaline-di-N-oxide |
| 66 | —CH$_3$/(F) | —F/(CH$_3$) | 6(7)-fluoro-7(6)-methyl-2-mercapto-3-hydroxy-quinoxaline-di-N-oxide |
| 67 | —OCH$_3$/(Cl) | —Cl/(OCH$_3$) | 6(7)-chloro-7(6)-methoxy-2-mercapto-3-hydroxa-quinoxaline-di-N-oxide |

EXAMPLE 68:
2-MERCAPTO-3HYDROXY-6(7)-FLUORO-7(6)-CHLOROQUINOXALINE-DI-N-OXIDE

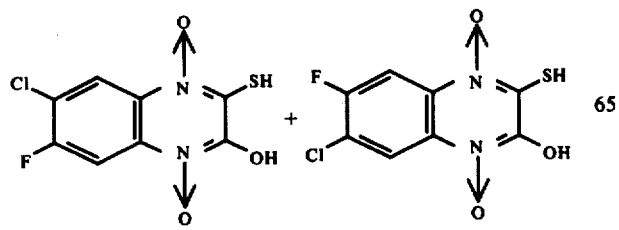

di-N-oxide, i.e. 2-mercapto-3-hydroxy-6(7)-chloro-quinoxaline-di-N-oxide having a decomposition point of 157° C.

EXAMPLE 69:
2-MERCAPTO-3-HYDROXY-6(7)-TRI-FLUOROMETHYL-7(6)-CHLOROQUINOXALINE-DI-N-OXIDE

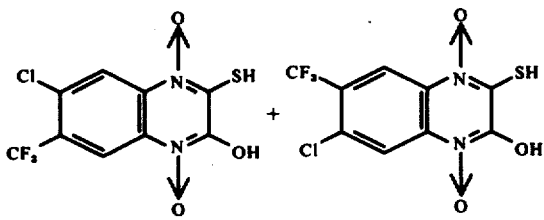

STEP A:
2-CYANO-3-HYDROXY-6(7)-TRIFLUOROMETHYL-7(6)-CHLOROQUINOXALINE-DI-N-OXIDE

Upon substituting an equivalent amount of 5-trifluoromethyl-6-chloro-benzofuroxane for the benzofuroxane of Example 44, Step A, and otherwise following the procedure described therein, there is thus obtained a mixture of 2-cyano-3-hydroxy-6-trifluoromethyl-7-chloro-quinoxaline-di-N-oxide and 2-cyano-3-hydroxy-6-chloro-7-trifluoromethyl-quinoxaline-di-N-oxide, i.e., 2-cyano-3-hydroxy-6(7)-trifluoromethyl-7(6)-chloro-quinoxaline-di-N-oxide.

STEP B:
2-MERCAPTO-3-HYDROXY-6(7)-TRIFLUOROMETHYL-7(6)-CHLORO-QUINOXALINE-DI-N-OXIDE upon substituting an equivalent amount of 2-cyano-3-hydroxy-6(7)-trifluoromethyl-7(6)-chloro-quinoxaline-di-N-oxide for the 2-cyano-3-hydroxy-quinoxaline-di-N-oxide of Example 44, Step B, and otherwise following the procedure described therein, there is thus obtained an approximately 1:1 mixture of 2-mercapto-3-hydroxy-6-trifluoromethyl-7-chloro-quinoxaline-di-N-oxide and 2-mercapto-3-hydroxy-6-chloro-7-trifluoromethyl-quinoxaline-di-N-oxide, i.e., 2-mercapto-3-hydroxy-6(7)-trifluoromethyl-7(6)-chloroquinoxaline-di-N-oxide having a decomposition point of 179° C.

The following example illustrates the use of the instant products as intermediates in preparing the 2-alkyl-thiolquinoxaline-di-N-oxide derivities of Br. Patent Specification No. 1,293,850. It is to be understood that this example is illustrative only and that in practice the alkylation procedure described therein can be employed in the conversion of all of the instant products (I) to their corresponding 2-alkyl-thio-quinoxaline-di-N-oxide derivatives.

EXAMPLE 70:
2-METHYLTHIO-3-METHYLQUINOXALINE-DI-N-OXIDE

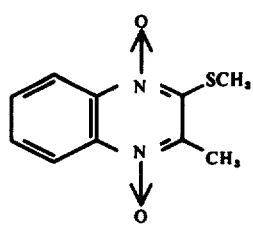

2-Mercapto-3-methyl-quinoxaline-di-N-oxide (208 g., 1.0 mol) and sodium hydroxide (40 g., 1.0 mol) are dissolved in water (1.0 liter) and dimethyl sulphate (139 g., 1.1 mole) is added dropwise at room temperature (about 20° C). The temperature is prevented from rising above 30° C by occasional cooling with ice water. After some time, yellow crystals of 2-methylthio-3-methylquinoxaline-di-N-oxide separate out and the said product is filtered to afford 200 g (90% of theoretical) of 2-methylthio-3-methylquinoxaline-di-N-oxide. Upon recrystallization from methanol the said product melts at 146°–148 C

What is claimed is:

1. Process for the preparation of a mercapto compound of the formula:

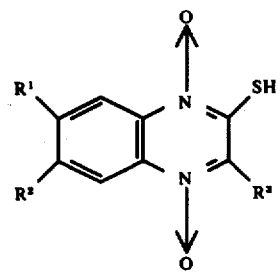

wherein each of $R^1$ and $R^2$ is hydrogen, lower alkyl, lower alkoxy, trifluoromethyl or halo and $R^3$ is methyl, hydroxy or amino which comprises treating a nitrile of the formula:

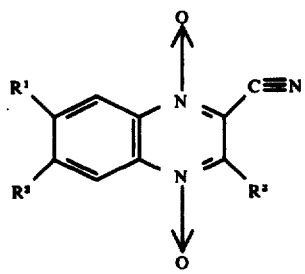

with hydrogen sulfide or an alkali metal or alkaline earth metal salt thereof in a solvent and, when a salt of hydrogen sulfide is used, converting the resultant mercaptide salt into the corresponding free mercapto compound by acidification with a nonoxidizing and nonreducing organic or inorganic acid.

2. A process according to claim 1, wherein the solvent is an alcohol, an alkyl nitrile or dialkylformamide.

3. A process according to claim 1, wherein $R^1$ and $R^2$ are the same or different and are each hydrogen, lower alkyl, lower alkoxy, chloro, fluoro or trifluoromethyl.

4. A process according to claim 1, wherein $R^1$ and $R^2$ are the same or different and are each hydrogen, methyl, methoxy, fluoro or trifluoromethyl.

5. A process according to claim 1, wherein $R^1$ and $R^2$ are the same or different and are each hydrogen, methyl, ethoxy or chloro.

6. A process according to claim 1, wherein hydrogen sulfide is used.

7. A process according to claim 1, wherein hydrogen sulfide is used in the form of an alkali metal sulfide.

8. A process according to claim 1 conducted at a temperature of from about 0° to about 150° C.

9. The process according to claim 7 wherein the alkali metal sulfide is sodium sulfide.

10. The process according to claim 9 for preparing 2-mercapto-3-methyl-(6)7-chloroquinoxaline-di-N-oxide wherein said nitrile is 2-cyano-3-methyl-(6)7-chloroquinoxaline-di-N-oxide.

11. The process according to claim 9 for preparing 2-mercapto-3-methyl-6(7)-ethoxyquinoxaline-di-N-oxide wherein said nitrile is 2-cyano-3-methyl-(6)7-ethoxyquinoxaline-di-N-oxide.

12. The process according to claim 9 for preparing 2-mercapto-3-methyl-6(7)-bromoquinoxaline-di-N-oxide wherein said nitrile is 2-cyano-3-methyl-6(7)-bromoquinoxaline-di-N-oxide.

13. The process according to claim 9 for preparing 2-mercapto-3-aminoquinoxaline-di-N-oxide wherein said nitrile is 2-cyano-3-aminoquinoxaline-di-N-oxide.

14. The process according to claim 9 for preparing 2-mercapto-3-amino-6(7)-chloroquinoxaline-di-N-oxide wherein said nitrile is 2-cyano-3-amino-6(7)-chloroquinoxaline-di-N-oxide.

15. The process according to claim 9 for preparing 2-mercapto-3-amino-6(7)-methylquinoxaline-di-N-oxide wherein said nitrile is 2-cyano-3-amino-6(7)-methylquinoxaline-di-N-oxide.

16. The process according to claim 9 for preparing 2-mercapto-3-hydroxy-quinoxaline-di-N-oxide wherein said nitrile is 2-cyano-3-hydroxy-quinoxaline.

17. The process according to claim 9 for preparing 2-mercapto-3-hydroxy-6(7)-fluoro-7(6)-chloroquinoxaline-di-N-oxide wherein said nitrile is 2-cyano-3-hydroxyl-6(7)-fluoro-7(6)-chloroquinoxaline-di-N-oxide.

18. The process according to claim 9 for preparing 2-mercapto-3-hydroxy-6(7)-trifluoromethyl-7(6)-chloroquinoxaline-di-N-oxide wherein said nitrile is 2-cyano-3-hydroxy-6(7)-trifluoromethyl-7(6)-chloroquinoxaline-di-N-oxide.

19. The process according to claim 9 for preparing 2-mercapto-3-methylquinoxaline-di-N-oxide wherein said nitrile is 2-cyano-3-methylquinoxaline-di-N-oxide.

20. A process according to claim 8 conducted at a temperature of from 20° to 40° C.

* * * * *